United States Patent [19]

Braquet et al.

[11] Patent Number: 5,116,992
[45] Date of Patent: May 26, 1992

[54] GLYCEROL DERIVATIVES, AND THERAPEUTICAL COMPOSITIONS CONTAINING THEM

[75] Inventors: Pierre Braquet, Garches; Colette Broquet, Boulogne; Bénédicte Vandamme, Versaille; Paola Principe-Nicolas, Paris, all of France

[73] Assignee: Societe de Conseils de Recherches et d'Applications Scientifiques (S.C.R.A.S.), France

[21] Appl. No.: 630,296

[22] Filed: Dec. 19, 1990

[30] Foreign Application Priority Data

Dec. 22, 1989 [GB] United Kingdom ............... 29074
Dec. 22, 1989 [GB] United Kingdom ............... 29075

[51] Int. Cl.⁵ ............................................. C07D 213/24
[52] U.S. Cl. ........................................ 514/77; 546/335; 546/22; 514/143; 514/148; 514/357; 514/476; 514/551; 558/169; 558/170; 558/172; 560/155; 560/159; 564/291; 554/105; 554/106
[58] Field of Search ............ 260/404, 405, 403, 404.5; 564/291; 558/170, 169; 514/143, 148, 357, 476, 551; 546/335; 560/155, 159

[56] References Cited

PUBLICATIONS

Chemical Abstracts, vol. 110, #14, 1988, 121101g.

*Primary Examiner*—Michael L. Shippen
*Assistant Examiner*—Deborah D. Carr
*Attorney, Agent, or Firm*—Lucas & Just

[57] ABSTRACT

The invention relates to glycerol derivatives of general formulae Ia, Ib and Ic

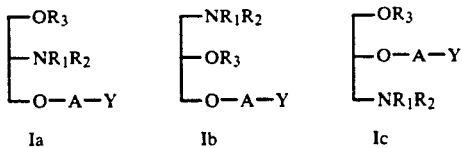

wherein $R_1$, $R_2$, $R_3$, A and Y stand for various substituents, to a preparation process of said compounds and to therapeutical compositions containing the same.

2 Claims, No Drawings

GLYCEROL DERIVATIVES, AND THERAPEUTICAL COMPOSITIONS CONTAINING THEM

The invention relates to glycerol derivatives which are of interest for their antitumoral activity, to a method for their preparation and to pharmaceutical compositions containing them.

The invention relates to glycerol derivatives of general formulae Ia, Ib and Ic

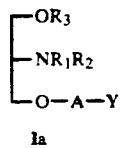   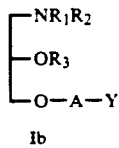   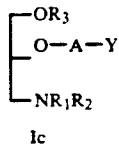

wherein:

$R_1$ represents a hydrogen atom or a lower alkyl group up to $C_5$;

$R_2$ represents a straight chain or branched chain alkyl group having from 10 to 24 carbon atoms;

$R_3$ represents an aryl or an alkyl radical, CONH-alkyl, CON-dialkyl, each alkyl group having from 1 to 6 carbon atoms;

A stands for:

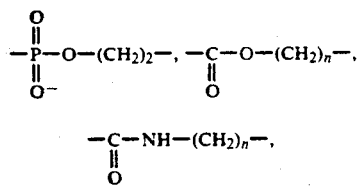

n being an integer of from 2 to 10;

Y represents the following quaternary ammonia: ammonium, alkylammonium, dialkylammonium, trialkylammonium, each alkyl group having from 1 to 6 carbon atoms, or a saturated or unsaturated heterocycle containing nitrogen atom as a hetero atom, and therapeutically acceptable salts thereof.

The invention relates, also, to a preparation process of glycerol derivatives Ia, Ib and Ic, comprising reacting, in an aprotic solvent, in presence of an organic base, at a temperature of from 0° to 80° C. and under nitrogen circulation, respectively the compounds of formulae IIa, IIb and IIc

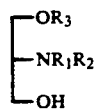 IIa

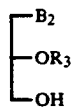 IIb

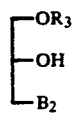 IIc wherein $R_1$, $R_2$, and $R_3$ are as above defined and $B_2$ represents $-NR_1'R_2$ or $-N(SO_2CH_2\phi)R_2$, wherein $R_1'$ stands for lower alkyl up to $C_5$;

with a stoichiometric excess of from 10 to 100% of a compound selected from within

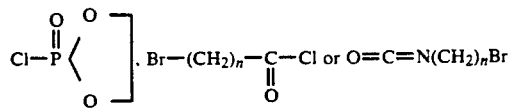

(n being as above defined) and with a stoichiometric excess of from 30 to 50% of a compound Z, selected from within an amine associated with the above defined quaternary ammonium of the above definition Y, and, for the obtention of compounds Ib or Ic, wherein $R_1$ stands for hydrogen, further hydrogenolysis of the protective group $-SO_2CH_2\phi$.

In some cases, the reactant Z may be also the solvent of the reaction; in such cases, the definition "a stoichiometric excess" becomes meaningless.

As the reaction is the same for the obtention of compounds Ia, Ib and Ic, it will be illustrated only for the compound Ia in the reaction scheme I.

Glycerol derivatives, and more particularly phosphocholine derivatives, have been already described for example in patent EP 130527; one of these related compounds, effective in cancer treatment, the 3-octadecylamino-1-o-tetradecylpropan-1,2-diol-2-o-phosphocholine, and a reference compound, the Et-18-OCH$_3$ (methoxy-PAF; Andreesen; 1988), have been retained for comparison purposes with the compounds of the invention. The results have shown that the compounds of the invention have a higher antitumoral activity, as evidenced in the pharmacological test herewith.

The invention relates, finally, to therapeutical compositions containing one of the compounds of the invention as an active ingredient, in admixture with appropriate diluents and/or carriers.

The different starting materials IIa, IIb and IIc may be prepared according the reaction schemes II, III, IV and V.

The starting material IIa may be prepared according reaction scheme II: the particularity of these reactions consists in the step 3a→4a the mechanism comprises 2

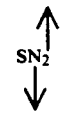

substitutions, with the $-OR_2$ and $-NR_1R_2$ groups migrating, as described by K. Suzuki, K. Okano in *Synthesis* 723 (Sep. 1983).

The starting material IIb may be prepared:

according to reaction scheme III: the compound IIb may comprise a protective group, when the final product Ib has $R_1$ as hydrogen. A deprotection by hydrogenolysis will be conducted on the final product;

according to reaction scheme IV, way A or B, specifically when $R_3$ represents $-$CONH-alkyl or $-$CON-dialkyl radical; the starting material 6b of reaction scheme IV is identical with compound 2a of reaction scheme II.

As regards the starting material IIc, reaction scheme V, please refer to starting material IIb, first paragraph.
These steps are below described in the following preparative examples.
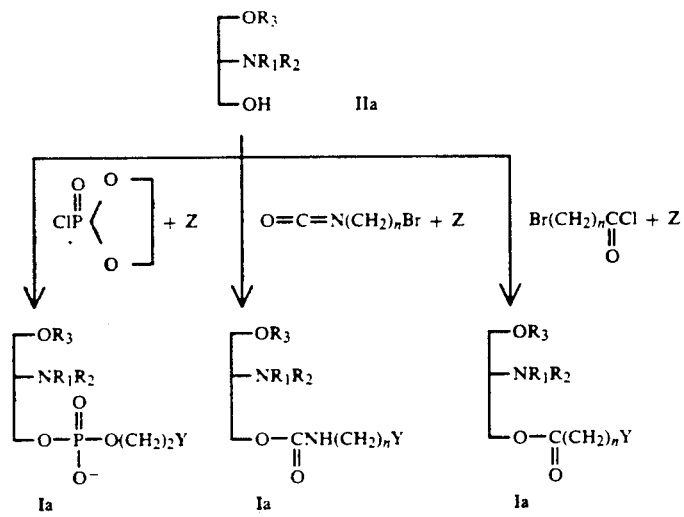
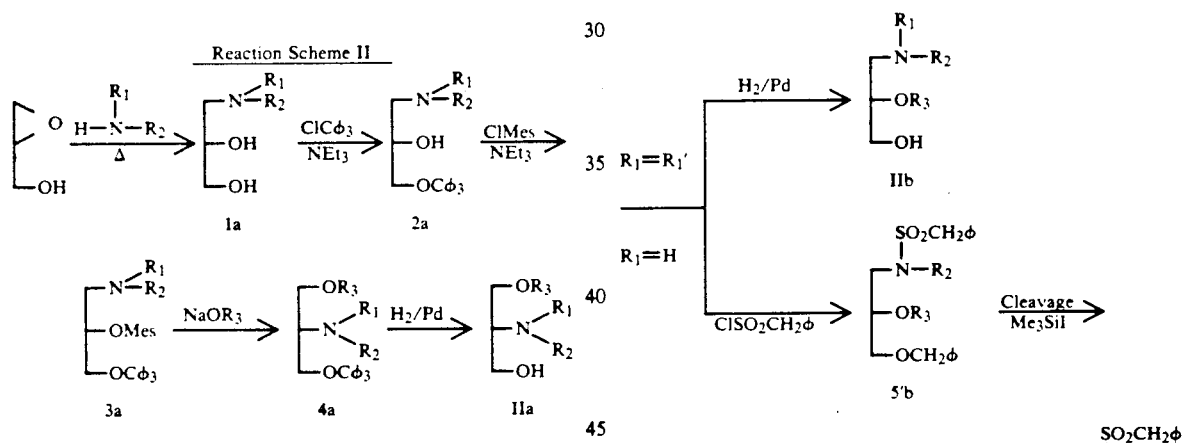
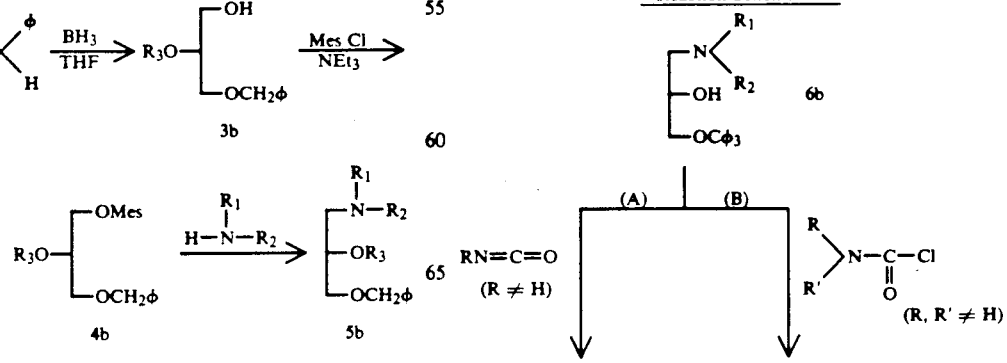

Reaction Scheme IV (continued)

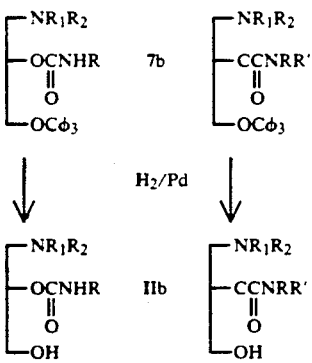

Reaction Scheme V

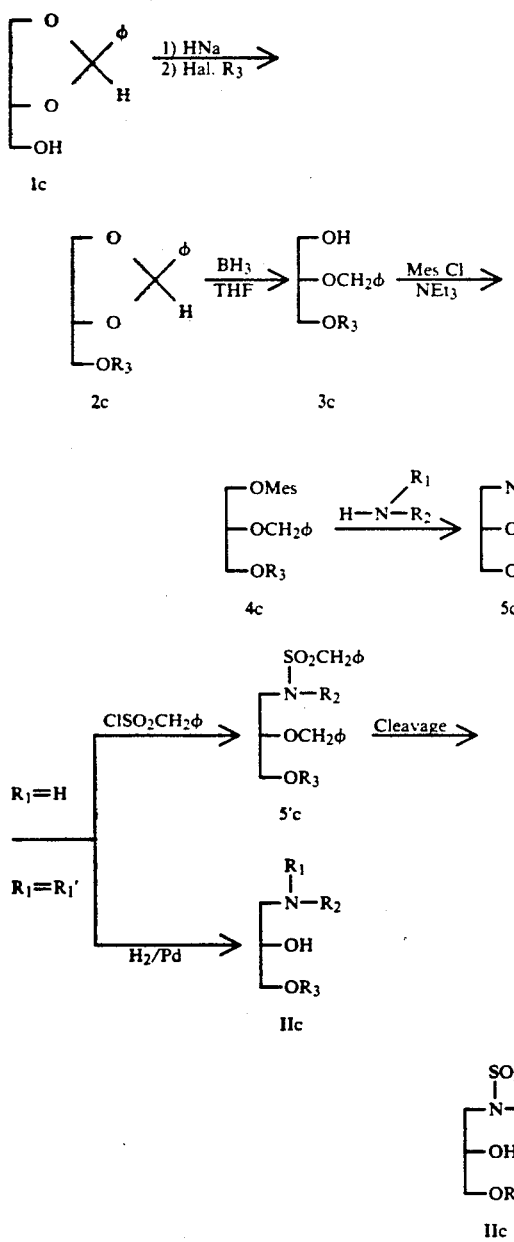

I. Preparative example of the starting material IIa, according to the reaction scheme II: $R_1=CH_3$, $R_2=C_{18}H_{37}$, $R_3=CH_3$

Step 1

3-(N-methyl-octadecylamino)-1,2-propanediol (1a)

A mixture of glycidol (4 ml, 60 mmol) and N-methyl-octadecylamine (16 g, 60 mmol) in dry toluene (50 ml) was refluxed under stirring for 3 hours. After evaporation of the solvent, the residue was crystallized to yield 16 g (84%) of the title compound. m.p. 59° C. (Hexane). M=357

TLC rf: 0.25 (CHCl$_3$/MeOH, 80:20 v/v)

IR (cm$^{-1}$) (nujol) 3300 (OH); 1090,1050 (C—O)

$^1$H-NMR: CDCl$_3$, δ (TMS) 300 MHz 0.82 (t, 3H, CH$_3$); 1.25 [s, 30H, (CH$_2$)$_{15}$]; 1.45 (t, 2H, NCH$_2$CH$_2$); 2.3 (s, 3H, NCH$_3$); 2.5 (m, 4H, CH$_2$—N—CH$_2$); 3.3 (large s., 1H, OH); 3.5 (m, 2H, H$_2$COH); 3.75 (m, 1H, CHOH).

Step 2

3-(N-methyl-octadecylamino)-1-trityloxy-propan-2-ol (2a)

50 mmol of 1a was treated for 12 hours with 60 mmol of trityl chloride and 120 mmol of triethylamine in 150 ml of boiling toluene. After conventional working up, the remaining oil was chromatographed (Flash chromatography, eluent chloroform) and gave 2a (yield 85%) m.p. 45° C.

TLC rf: 0.44 (CHCl$_3$/MeOH 95:5 v/v)

IR (cm$^{-1}$) 3500 (OH); 3080, 3050, 3020 (ArCH); 1600 (C=C); 1080 (C—O)

$^1$H-NMR: 300 MHz, CDCl$_3$, δ (TMS) 2.3 (s, 3H, NCH$_3$); 2.5 (m, 4H, CH$_2$—N—CH$_2$); 3.2 (2m, 2H, CH$_2$Otrityl); 3.9 (m, 1H, H-COH); 7.3, 7.5 (m, 15H, trityl).

Step 3

3-(N-methyl-octadecylamino)-2-methanesulphonyloxy-1-trityloxy-propane (3a)

18 g (30 mmol) of 2a was dissolved in 100 ml of dry diethyl ether and 50 ml of dichloromethane. 6.84 g (60 mmol) of methanesulphonyl chloride in 50 ml of dichloromethane was added under stirring, and the mixture was refluxed for 5 hours. Water was then added, and the organic phase was decanted, dried and evaporated. The crude product was chromatographed (eluent as in Step 2), yielding 16.7 g of 3a (80%).

M=677

TLC rf: 0.25 (CHCl$_3$)

IR (cm$^{-1}$) 1600 (C=C); 1370, 1180 (SO$_2$); 1080 (C—O)

$^1$H-NMR: 300 MHz CDCl$_3$ 2.2 (s, 3H, NCH$_3$); 2.4 (m, 2H, NCH$_2$); 2.65 (m, 2H, CH$_2$N); 3 (s, 3H, CH$_3$SO$_2$); 3.35 (m, 2H, CH$_2$OTr); 4 (m, 1, CHOSO$_2$).

Step 4

3-methoxy-2-(N-methyl-octadecylamino)-1-trityloxy propane (4a)

This compound was prepared by reacting 3a with sodium methoxide. Yield 68%.

M=613

TLC rf: 0.42 (CHCl$_3$/MeOH); 98:2 ; v/v)

IR (cm$^{-1}$) 1120 (C—O—Me) 1050 (C—O)

¹H-NMR: 300 MHz CDCl₃ δ (TMS) 2.2 (s, 3H, NCH₃); 2.4 (m, 2H, NCH₂); 3.05 (quintet, 1H, CHN); 3.3 (s, 3H, OCH₃); 3.35 (d, 2H, C$\underline{H}$₂OCH₃); 3.6 (d, 2H, CH₂OTr).

Step 5

3-methoxy-2-(N-methyl-octadecylamino)-propanol (IIa)

This compound was obtained by hydrogenolysis for 5 hours at 40° C. at 40 psi (275880 pascals) of 4a in chloroform, using 10% palladium-on-charcoal as catalyst.

TLC rf: 0.17 (CHCl₃/MeOH; 95:5; v/v) M = 399.

IR (cm⁻¹) 3410 (OH); 1120 (C—O—Me); 1050 (C—O—C)

¹H-NMR: 300 MHz. δ 2.25 (s, 3H, N—CH₃); 2.5 (m, 2H, NCH₂); 3 (m, 1H, CHN); 3.30 (m, 3H, CH₂OCH₃, OH); 3.35 (s, 3H, OCH₃); 3.6 (m, 2H, CH₂O$\underline{H}$).

II. Preparative example of the starting material IIb according to reaction scheme III: R₁=CH₃, R₂=C₁₈H₃₇, R₃=CH₃

Step 2

2-phenyl-5-methoxy-1,3-dioxane (2b)

2-phenyl-5-hydroxy-1,3-dioxane 1b was obtained according to Verkaade P. E. and Van Roon J. D. (Rec. Trav. Chim. Pays-Bas, 61, 831, 1942). m.p. 80° C.

10 g of the sodium salt of 1b, obtained by reaction with sodium hydride in dimethylformamide, was treated with 16 g of methyl iodide. The mixture was stirred at 50° C. for 5 hours, and the dimethylformamide was eliminated in vacuo. The residue was dissolved in dichloromethane, washed and dried. The solvent was evaporated off and the product was chromatographed on silica gel (eluent : dichloromethane) to give 2b.

Yield 75%
mp: 51° C.; M = 194
TLC rf: 0.32 (petroleum ether/diethyl ether 50:50)
IR (cm⁻¹) 3100, 3060, 3040 (CH,φ), 1600 (C=C), 1100 (C—O)
¹H-NMR: 60 MMz, CDCl₃ TMS (δ) 3.4(s, 3H, OCH₃); 3.8 (s, 1H, HCOMe); 4 (m, 4H, CH₂—O); 5.5 (s, 1H,

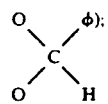

7.4 (m, 5H, φ).

Step 3

3-benzyloxy-2-methoxy-propanol (3b)

4.2 g of 2b was dissolved in 10 ml of tetrahydrofuran at 0° C. A solution of BH₃ in tetrahydrofuran (1M, 30 ml) was added slowly, under stirring. Stirring was continued for 48 hours at room temperature. The mixture was then cooled to 0° C., quenched with cold water and extracted with diethyl ether. The solvent was eliminated and the crude product was chromatographed (eluent petroleum ether/diethyl ether, successively 80:20 and 70:30 by volume), yielding 2.6 g of 3b (62%).

TLC rf: 0.23 (petroleum ether/diethyl ether 50:50 v/v) viscous. M = 196

IR (cm⁻¹) 3400 (OH) 3100—3060—3040 (CH,φ) 1600 (C=C) 1100 (C—O)

¹H-NMR: CDCl₃, TMS. (δ) 60 MHz 2.6 (1H, OH); 3.4 (s, 3H, OCH₃); 3.5 (m, 5H, glycerol); 4.5 (s, 2H, CH₂ φ); 7.3 (5H, φ).

Step 4

3-benzyloxy-2-methoxy-1-methanesulphonyloxy-propane (4b)

To a solution of 5.88 g (30 mmol) of 3b and 10 ml of triethylamine in 100 ml of dry diethyl ether and 50 ml of dichloromethane, was added under stirring 6.84 g (60 mmol) of methanesulphonyl chloride in 50 ml of dichloromethane, and the mixture was refluxed for 5 hours. Water was then added, and the organic phase was decanted, dried and evaporated. The crude product was chromatographed (eluent petroleum ether/diethyl ether 80:20 by volume), to yield 6 g (74%) of 4b.

TLC rf: 0.35 (CHCl₃) viscous. M = 274

IR (cm⁻¹) 1600 (C=C); 1350 (SO₂); 1170 (SO₂); 1100 (C—O—) ¹H-NMR: CDCl₃, TMS (δ) 60 MHz 3 (s, 3H, SO₂CH₃); 3.4 (s, 3H, OMe); 3.5 (d, 2H, CH₂OCH₂ φ); 3.8 (m, 1H, HCOMe); 4.4 (m, 2H, C$\underline{H}$₂OSO₂); 4.6 (s, 2H, CH₂φ); 7.4 (5H, φ).

Step 5

3-benzyloxy-2-methoxy-N-methyl-N-octadectyl-propylamine (5b)

5.4 g (20 mmol) of 4b was dissolved in 15 ml of dimethylsulphoxide and added to a solution of 5.7 g (20 mmol) of N-methyl-octadecylamine and 1.4 ml of triethylamine in 60 ml of dimethylsulphoxide. The mixture was stirred at 80° C. for 24 hours. The dimethylsulphoxide was eliminated. The residue was dissolved in dichloromethane, washed with water and dried. The crude product was chromatographed (eluent dichloromethane:methanol 98:2 by volume), yielding 4.2 g of 5b (46%).

TLC rf: 0.42 (CH₂Cl₂/MeOH 95:5, v/v) viscous. M = 461

IR (cm⁻¹) 1100 (C—O—)

¹H-NMR: CDCl₃, TMS (δ) 60MHz 0.9 (t, 3H, CH₃); 1.25 (large sing, 32H); 2.3 (s, 3H, NCH₃); 2.6 (m, 4H, CH₂—N—CH₂); 3.45 (s, 3H, OCH₃); 3.6 (m, 3H, CHOMe and CH₂OCH₂φ); 4.6 (s, 2H, CH₂ φ); 7.4 (5H, φ).

Step 6

3-(N-methyl-octadecylamino)-2-methoxy-propanol (IIb)

This compound was obtained by hydrogenolysis for 5 hours at 40° C. at 40 psi (275880 pascals) of 5b in chloroform, using 10% palladium-on-charcoal as catalyst.

TLC rf: 0.35 (CH₂Cl₂/MeOH, 95:5, v/v). M = 371

IR (cm⁻¹) 3450 (OH); 1110 (C—O—Me); 1060 (C—OH)

¹H-NMR: 60MHz, CDCl₃, δ 2.3 (s, 3H, NCH₃); 2.6 (m, 4H, CH₂NCH₂); 3.45 (s, 3H, OCH₃); 3.6 (m, 3H, C$\underline{H}$OMe and CH₂OH); 5.3 (1H, OH).

III. Preparative example of the starting material IIb according to reaction scheme III: R₁=CH₃, R₂=C₁₈H₃₇, R₃=C₂H₅

The procedure was the same as described in the preparative example II.

Step 2

2-phenyl-5-ethoxy-1,3-dioxane (2b)

yield: 70%
TLC rf: 0.74 (CH$_2$Cl$_2$/MeOH, 98:2, v/v)

Step 3

3-benzyloxy-2-ethoxy-propanol (3b)

yield: 78%
TLC rf: 0.47 (CH$_2$Cl$_2$/MeOH, 98:2, v/v)

Step 4

3-benzyloxy-2-ethoxy-1-methanesulphonyloxy-propane (4b)

yield: 71%
TLC rf: 0.59 (CH$_2$Cl$_2$/MeOH, 99:1, v/v)

Step 5

3-benzyloxy-2-ethoxy-N-methyl-N-octadecyl propylamine (5b)

yield: 61%
TLC rf: 0.44 (CH$_2$Cl$_2$/MeOH, 95:5, v/v)

Step 6

3-(N-methyl-octadecylamino)-2-ethoxy-propanol (IIb)

yield: 92%
TLC rf: 0.32 (CH$_2$Cl$_2$/MeOH, 95:5, v/v)

IV. Preparative example of the starting material IIb according to reaction scheme III: $R_1 = H$, $R_2 = C_{18}H_{37}$, $R_3 = CH_3$ The procedure of the steps 1 to 4 is the same as described in the preparative example II, steps 1 to 4.

Step 5

3-octadecylamino 2-methoxy 1-benzyloxy propane (5b)

The procedure is the same as step 5, preparative example II, using octadecylamine instead of N-(methyl)octadecylamine.
TLC rf: 0.39 (CH$_2$Cl$_2$/MeOH, 95/5, v/v).

Step 6

Protection of the amino-group 3-N,N-(benzylsulphonyl octadecyl)amino 2-methoxy 1-benzyloxypropane (5'b)

The compound 5'b was obtained by reaction of benzylsulfonyl chloride on 5b in the presence of NEt$_3$ with CH$_2$Cl$_2$ as solvent, at room temperature for 24 hours.
IR (cm$^{-1}$) 1350 and 1190 (SO$_2$)

Step 7

3-N,N-(benzylsulphonyl octadecyl)amino 2-methoxy propan-1-ol (IIb)

The benzyl group was cleaved using Me$_3$SiI in CH$_2$Cl$_2$ at room temperature for 20 minutes.
TLC rf: 0.21 (hexane, ethylacetate 70:30 v/v).

V. Preparative example of the starting material IIb according to reaction scheme IV, way A: $R_1 = CH_3$, $R_2 = C_{18}H_{37}$,

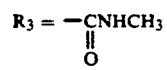

Step 1

3-(N-methyl octadecylamino)-2-methylcarbamoyloxy-1-trityloxy propane (7b)

The preparation of 3-(N-methyl octadecylamino) 1-trityloxypropan-2-ol 6b is illustrated in the preparative example I, step 2.

A solution of 3-(N-methyl octadecylamino) 1-trityloxypropan-2-ol 6b (6 10$^{-3}$ M), pyridine (1 ml) and methylisocyanate (1.2 ml) in dry benzene (45 ml), was heated at 40° C. for three days. After elimination of the solvent, the residue was purified by column chromatography with CH$_2$Cl$_2$ as eluent, to give 7b.
Yield: 80% M=661
TLC rf: 0.65 (CHCl$_3$/MeOH, 98:2, v/v)
IR (cm$^{-1}$) 3350 (NH); 3080, 3050, 3020 (ArCH), 1695 (C=O); 1600 (C=C)
$^1$H-NMR: 60 MHz, CDCl$_3$, TMS, δ
2.8 (d, 3H, CONHCH$_3$); 3.4 (m, 2H, CH$_2$OTr); 4.8 (m, 1H, CONHCH$_3$); 5 (m, 1H, HCOCON)

Step 2

3-(N-methyl octadecylamino)-2-methylcarbamoyloxy propan-1-ol (IIb)

This compound was obtained by hydrogenolysis of 7b.
TLC rf: 0.35 (CHCl$_3$/MeOH, 90:10, v/v)
M=414
$^1$H-NMR: 60 MHz, CDCl$_3$, TMS, δ 1.8 (1H, OH); 3.8 (d, 2H, CH$_2$OH); 5 (m, 1H, HCOCON); 6.4 (1H, CONHCH$_3$)

VI. Preparative example of the starting material IIb according to reaction scheme IV, way B: $R_1 = CH_3$,

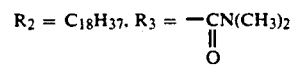

Step 1

3-(N-methyl octadecylamino) 2-[N,N-(dimethyl)carbamoyloxy]-1-trityloxy-propane (7b)

A solution of 3-(N-methyl octadecylamino)- 1-trityloxy propan-2-ol 6b (5.4 mmol) and 1.4 g (13.5 mmol) of dimethylcarbamoyl chloride in 30 ml of pyridine, was refluxed for three days. After elimination of pyridine, the residue was dissolved in dichloromethane, washed and dried. The solvent was evaporated and the crude product chromatographed on silica gel to yield 1.53 g (42%) of 7b.
M=675
TLC rf: 0.1 (CH$_2$Cl$_2$/MeOH, 91:1, v/v)
IR (cm$^{-1}$) 1700 (C=O); 1600 (C=C)
$^1$H-NMR: 60 MHz, CDCl$_3$, TMS, δ 2.3 (s, 3H, NCH$_3$); 2.4 (m, 2H, NCH$_2$); 2.6 (m, 2H, CH$_2$N); 2.8 [s, 6H, CON(CH$_3$)$_2$]; 3.3 (m, 2H, CH$_2$Otrityl); 7.3 (m, 15H, trityl)

Step 2

3-(N-methyl octadecylamino)-2-[N,N-(dimethyl)carbamoyloxy]propan-1-ol (IIb)

The compound IIb was obtained by hydrogenolysis of 7b.

M = 428

TLC rf: 0.43 ($CH_2Cl_2$/MeOH, 90:10, v/v)

IR ($cm^{-1}$) 1700 (C=O)

$^1$H-NMR: 60 MHz, $CDCl_3$, TMS, δ 2.9 [s, 6H, $N(CH_3)_2$]; 3.8 (d, 2H, $CH_2$OH); 4 (1H, OH); 4.9 (m, 1H, HCOCON)

VII. Preparative example of the starting compound IIc, according to the reaction scheme V: $R_1 = CH_3$, $R_2 = C_{18}H_{37}$, $R_3 = CH_3$

Step 1

2-phenyl-4-methoxymethyl-1,3-dioxolan (2c)

This compound was obtained by the same procedure as described in preparative example II, step 2 but starting from 2-phenyl-4-hydroxymethyl-1,3-dioxolan 1c instead of 2-phenyl-5-hydroxy-1,3-dioxane 1b. Yield 75%. Viscous product.

TLC rf: 0.60 ($CH_2Cl_2$/MeOH, 98:2 v/v)

$^1$H-NMR: $CDCl_3$, TMS, 60MHz δ: 3.35 (s, 3H, $OCH_3$); 3.6 (m, 2H, $CH_2OCH_3$); 3.9 (m, 3H, $CH_2O$, CHO); 5.8

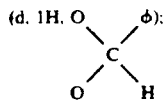

7.4 (m, 5H, φ).

Step 2

3-methoxy-2-benzyloxy-propanol (3c)

This compound was obtained by the same procedure as described in preparative example II, step 3, but starting from 2-phenyl-4-methoxymethyl-1,3-dioxolan 2c instead of 2-phenyl-5-methoxy-1,3-dioxane 2b.

Yield: 71%

TLC rf: 0.23 (petroleum ether/diethylether, 50:50 v/v)

$^1$H-NMR: $CDCl_3$, TMS, 60MHz, δ 2.5 (1H, OH); 3.3 (s, 3H, $OCH_3$); 3.6 (m, 5H, glycerol backbone); 4.6 (s, 2H, $CH_2$ φ); 7.3 (5H, φ).

Step 3

3-methoxy-2-benzyloxy-1-methanesulphonyloxy-propane (4c)

This compound was obtained by the same procedure as described in preparative example II, step 4, but starting from 3-methoxy-2-benzyloxy-propanol 3c instead of 3-benzyloxy-2-methoxy-propanol 3b.

Yield: 64%

TLC rf: 0.35 ($CHCl_3$)

$^1$H-NMR: $CDCl_3$, TMS, 60MHz, δ 3 (s, 3H, $SO_2CH_3$); 3.4 (s, 3H, $OCH_3$); 3.5 (d, 2H, $CH_2OCH_3$); 3.8 (m, H, HC—$OCH_2$φ); 4.4 (m, 2H, $CH_2OSO_2$); 4.65 (s, 2H, $CH_2$φ); 7.3 (5H, φ).

Step 4

3-methoxy-2-benzyloxy-N-methyl-N-octadecyl-propylamine (5c)

This compound was obtained by the same procedure as described in preparative example II, step 5, but starting from 3-methoxy-2-benzyloxy-1-methanesulphonyloxy-propane 4c instead of 3-benzyloxy-2-methoxy-1-methanesulphonyloxy-propane 4b.

Yield: 50%

TLC rf: 0.42 ($CH_2Cl_2$/MeOH, 95:5, v/v)

$^1$H-NMR: 60MHz, δ 0.9 (t, 3H, $CH_3$); 1.3 (large s, 32H); 2.3 (s, 3H, $NCH_3$); 2.5 (m, 4H, $CH_2NCH_2$); 3.4 (s, 3H, $OCH_3$); 3.6 (m, 3H, $CH_2$OMe, $CH$OCH$_2$φ); 4.7 (s, 2H, $CH_2$φ); 7.3 (5H, φ).

Step 5

3-(N-methyl-octadecylamino)-1-methoxy-propan-2-ol (IIc)

This compound was obtained by hydrogenolysis of 5c under the conditions described in preparative example II, step 6.

Yield: 90%

TLC rf: 0.35 ($CH_2Cl_2$/MeOH, 95:5, v/v)

VIII. Preparative example of the starting compound IIc, according to the reaction scheme V: $R_1 = H$, $R_2 = C_{18}H_{37}$, $R_3 = CH_3$ The steps 1 to 3 are the same as described in preparative example VII, steps 1 to 3.

Steps 4 to 6

The procedure of preparation of 3-methoxy-2-benzyloxy-N-octadecyl propylamine (5c), of the protection reaction of the amino-group to obtain 3-methoxy-2-benzyloxy-N-(benzylsulfonyl octadecyl)propylamine (5'c) and of the cleavage of the benzyl group, was the same as described in preparative example IV, steps 5 to 7.

The invention will be better understood from the description of the following examples.

EXAMPLE 1

3-methoxy-2-(N-methyl-octadecylamino)-propanol phosphocholine

Compound of the formula Ia wherein $R_1 = CH_3$, $R_2 = C_{18}H_{37}$, $R_3 = CH_3$,

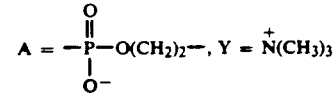

2 g (5 mmol) of 3-methoxy-2-(N-methyl-octadecylamino)propanol (IIa) and 3 ml of triethylamine were dissolved in 20 ml of dry benzene, and the mixture was cooled to 5° C. under nitrogen circulation. 1 g (7 mmol) of 2-chloro-2-oxo-1,3,2-dioxaphospholane in 4 ml of benzene was added under stirring, and stirring was continued overnight. The amino salt was filtered off and washed with benzene. The filtrate was evaporated to dryness under reduced pressure. The residue was dissolved in 20 ml of dry methyl cyanide and transferred to a reactor. 20 ml of methyl cyanide, saturated with gaseous trimethylamine, was added, and the mixture was heated at 65° C. for 24 hours. A solid separated on cooling. It was filtered off and chromatographed on silica gel (eluent chloroform:methanol 90:10, then 70:30 by volume, then methanol) to yield 1.1 g (39%) of the title compound.

M=564 m.p. 244° C.

TLC rf: 0.256 (CHCl$_3$/MeOH/NH$_4$OH; 70:30:7, v/v/v)

IR (cm$^{-1}$) 1240 (P=O); 1090 (C—O); 1040 (P—O—)

$^1$H-NMR: 500 MHz CD$_3$OD (TMS) δ 0.8 (t, 3H, CH$_3$); 1.25 [large s, 30H, (CH$_2$)$_{15}$]; 1.45 (t, 2H, NCH$_2$CH$_2$); 2.3 (s, 3H, NCH$_3$); 2.45 (m, 2H, NCH$_2$); 2.9 (m, 1H, CH$_2$N); 3.3 (s, 3H, OCH$_3$); 3.35 [s, 9H, N$^+$(CH$_3$)$_3$]; 3.5 (m, 2H, CH$_2$OCH$_3$); 3.7 (m, 2H, CH$_2$N$^+$); 3.95 (m, 2H, CH$_2$OP); 4.25 (m, 2H, POCH$_2$).

EXAMPLE 2

3-methoxy 2-(N-methyl)octadecylamino 1-[6'-(N-pyridinium) hexanoyloxy]propane bromide Compound of the formula Ia wherein R$_1$=CH$_3$, R$_2$=C$_{18}$H$_{37}$, R$_3$=CH$_3$,

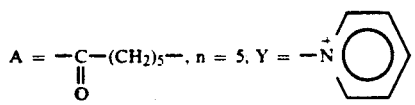

3-methoxy-2-(N-methyl-octadecylamino)-propanol (IIa) (3.5 g, 9 mmol) and Et$_3$N (25 mmol) in 15 ml of ethanol free chloroform, were added dropwise to a solution of 5-bromohexanoyl chloride (10 mmol) in 10 ml of the same solvent, at 0° C. under nitrogen circulation. The mixture was stirred for 15 hours at room temperature. After evaporation of solvent, 30 ml of dry pyridine was added to the obtained residue, and the mixture was then stirred at 80° C. under N$_2$ for 24 hours. Pyridine was eliminated in vacuo and the residue was purified by column chromatography (eluent CHCl$_3$ then CHCl$_3$/MeOH 90:10) to yield 2.47 g (70%) of the title compound.

M=627

TLC rf 0.19 (CHCl$_3$/MeOH, 70:30, v/v)

IR (cm$^{-1}$) 1740 (C=O); 1640 (pyridine)

$^1$H-NMR: 500 MHz, CDCl$_3$, TMS δ 1.4 (m 2H, COCH$_2$CH$_2$CH$_2$); 1.6 (m, 2H, COCH$_2$CH$_2$); 2.1 (m, 2H, CH$_2$CH$_2$—N$^+$); 2.35 (t, 2H, COCH$_2$); 5.05 (t, 2H, CH$_2$N$^+$); pyridinium 8.1 (t, 2H, H$_\beta$); 8.6 (d, 1H, H$_\gamma$); 9.5 (d, 2H, H$_\alpha$).

EXAMPLE 3

3-methoxy 2-(N-methyl)octadecylamino 1-[5'-(N-pyridinium) pentylcarbamoyl]propane bromide Compound of the formula Ia wherein R$_1$=CH$_3$, R$_2$=C$_{18}$H$_{37}$, R$_3$=CH$_3$,

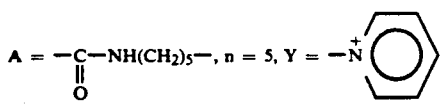

A mixture of 3-methoxy-2-(N-methyl-octadecylamino)-propanol (IIa) (3.5 g, 9 mmol), 5-bromopentylisocyanate (12 mmol) and 30 ml of pyridine, was heated for two days at 80° C. under nitrogen circulation. Pyridine was eliminated in vacuo and the obtained residue was dissolved in CHCl$_3$, washed and dried. The solvent was evaporated and the residue was chromatographed (eluent CHCl$_3$ then CHCl$_3$/MeOH, 95:5, 90:10) to yield 2.1 g (40%) of the title compound.

M=642

TLC rf: 0.23 (CHCl$_3$/MeOH, 70:30, v/v)

IR (cm$^{-1}$) 3350 (NH), 1720. CONH), 1640 (pyridine)

$^1$H-NMR: 500 MHz, CDCl$_3$, TMS δ 1.4 (m, 2H, COCH$_2$CH$_2$CH$_2$); 1.6 (m, 2H, COCH$_2$CH$_2$); 2.1 (m, 2H, CH$_2$—CH$_2$—N$^+$); 3.25 (t, 2H, CONHCH$_2$); 5.05 (t, 2H, CH$_2$N$^+$); 5.6 (NH); pyridinium 8.1 (t, 2H, H$_\beta$); 8.6 (d, 1H, H$_\gamma$); 9.5 (d, 2H, H$_\alpha$).

EXAMPLE 4

3-(N-methyl-octadecylamino)-2-methoxy-propanol phosphocholine

Compound of the formula Ib wherein R$_1$=CH$_3$, R$_2$=C$_{18}$H$_{37}$, R$_3$=CH$_3$

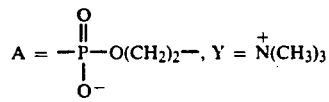

This compound was prepared by the same method as described in example 1, but starting with 3-(N-methyl-octadecylamino)-2-methoxy-propanol(IIb), instead of 3-methoxy-2-(N-methyl-octadecylamino)-propanol (IIa).

Yield: 46% M=564

TLC rf: 0.22 (CHCl$_3$/MeOH/NH$_4$OH, 70:30:7, v/v/v)

IR (cm$^{-1}$) 1240 (P=O); 1100 (C—O—); 1040 (P—O).

$^1$H-NMR: 500 MHz, CD$_3$OD, TMS (δ) 0.9 (t, 3H, CH$_3$); 1.25 [large s, 30H, (CH$_2$)$_{15}$]; 1.5 (m, 2H, NCH$_2$CH$_2$); 2.27 (s, 3H, NCH$_3$); 2.4 (m, 2H, NCH$_2$); 2.55 (m, 2H, CH$_2$N); 3.2 [s, 9H, N$^+$ (CH$_3$)$_3$]; 3.45 (s, 3H, OCH$_3$); 3.55 (m, 1H, CHOCH$_3$); 3.65 (t, 2H, CH$_2$N$^+$); 3.9 (m, 2H, CH$_2$OP); 4.3 (m, 2H, POCH$_2$).

EXAMPLE 5

3-(N-methyl-octadecylamino)-2-ethoxy-propan-1-ol phosphocholine

Compound of the formula Ib wherein R$_1$=CH$_3$, R$_2$=C$_{18}$H$_{37}$, R$_3$=C$_2$H$_5$,

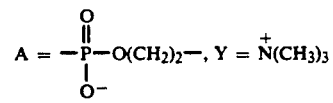

This compound was prepared by the same procedure as described in example 1, but starting with 3-(N-methyl-octadecylamino)-2-ethoxy-propanol IIb instead of 3-methoxy-2-(N-methyl-octadecylamino) propanol IIa.

Yield: 32% MH$^+$=579

TLC rf: 0.195 (CHCl$_3$/MeOH/NH$_4$OH, 70:30:7, v/v/v)

$^1$H-NMR: 500 MHz, CD$_3$OD, TMS, δ 0.9 (2t, 6H, 2CH$_3$); 1.25 [large s, 30H, (CH$_2$)$_{15}$]; 1.5 (m, 2H, NCH$_2$CH$_2$); 2.27 (s, 3H, NCH$_3$); 2.4 (m, 2H, NCH$_2$); 2.55 (m, 2H, CH$_2$N); 3.2 [s, 9H, N$^+$(CH$_3$)$_3$]; 3.55 (m, 1H, CHOCH$_3$); 3.65 (t+q, 4H, CH$_2$N$^+$ +OCH$_2$); 3.9 (m, 2H, CH$_2$OP); 4.3 (m, 2H, POCH$_2$).

EXAMPLE 6

3-octadecylamino 2-methoxy propan-1-ol phosphocholine

Compound of the formula Ib wherein $R_1=H$, $R_2=C_{18}H_{37}$, $R_3=CH_3$,

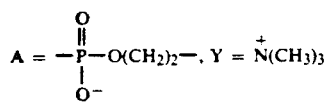

$$A = -\overset{O}{\underset{\underset{O^-}{|}}{\overset{\|}{P}}}-O(CH_2)_2-, \quad Y = \overset{+}{N}(CH_3)_3$$

3-N,N-(benzylsulphonyl octadecyl)amino 2-methoxy propan-1-ol phosphocholine

This compound was obtained by the same procedure as described in example 1, but starting with 3-N,N-(benzylsulphonyl octadecyl)amino 2-methoxy propan-1-ol (IIb) instead of 3-methoxy-2-(N-methyl-octadecylamino)-propanol (IIa).

Yield: 35%

TLC rf: 0.29 (CHCl$_3$/MeOH/NH$_4$OH, 70:30:7, v/v/v)

$_1$HNMR: 500 MHz, CD$_3$OD, TMS (δ) 3.15 [s+m, 12H, N$^-$(CH$_3$)$_3$ and

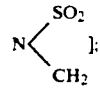

$$N \overset{SO_2}{\underset{CH_2}{\diagdown}} ];$$

3.35 (s+m, 5H, OCH$_3$ and CH$_2$N—SO$_2$); 3.55 (m, 3H, CHOCH$_3$ and CH$_2$N$^+$); 4.3 (m, 2H, POCH$_2$); 4.4 (m, 4$\overline{\text{H}}$, CH$_2$OP and SO$_2$CH$_2$φ); 7.40 (5H, φ).

3-octadecylamino 2-methoxy propan-1-ol phosphocholine

Deprotection reaction:

This compound was obtained by hydrogenolysis of 3-N,N-(benzylsulphonyl octadecyl)amino 2-methoxy propan-1-ol phosphocholine, using Raney-Nickel as catalyst.

TLC rf: 0.17 (CHCl$_3$/MeOH/NH$_4$OH, 70:30:7, v/v/v)

M=550

$^1$H-NMR: 500 MHz, CD$_3$OD, TMS (δ) 3 (m, 2H, NCH$_2$); 3.15 (m, 3H, NH and CH$_2$N); 3.45 [s, 9H, N$^+$(CH$_3$)$_3$]; 3.65 (s, 3H, OCH$_3$); 3.8 (m, 3H, CHOCH$_3$ and CH$_2$N$^+$); 4.2 (m, 2H, POCH$_2$); 4.4 ($\overline{\text{m}}$, 2H, CH$_2$OP).

EXAMPLE 7

3-(N-methyl octadecylamino)-2-methylcarbamoyloxy-propan-1-ol phosphocholine

Compound of the formula Ib wherein $R_1=CH_3$, $R_2=C_{18}H_{37}$,

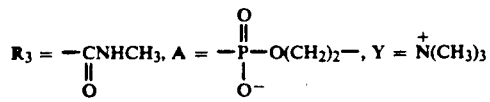

$$R_3 = -\overset{O}{\underset{\|}{\overset{\|}{C}}}NHCH_3, \quad A = -\overset{O}{\underset{\underset{O^-}{|}}{\overset{\|}{P}}}-O(CH_2)_2-, \quad Y = \overset{+}{N}(CH_3)_3$$

To a cooled (5° C.), stirred solution of 3-(N-methyl octadecylamino)-2-methylcarbamoyloxy propan-1-ol (IIb) (2.9 g, 7 mmol) and 3 ml of NEt$_3$ in dry benzene (20 ml), was added 2-chloro 2-oxo 1,3,2-dioxaphospholane (2 g, 14 mmol) in benzene (4 ml) under nitrogen circulation. The mixture was stirred at room temperature for 8 hours, then filtered. The filtrate was evaporated off under reduced pressure. The residue was dissolved in dry CH$_3$CN (50 ml) and transferred to a reactor. 30 ml of CH$_3$CN saturated by gaseous NMe$_3$ were added and the mixture was heated at 65° C. for 24 hours. The solvent was evaporated and the residue was chromatographed on silica gel (eluent CHCl$_3$/MeOH, 90:10 then 70:30 and 30:70, then methanol) to yield 1.74 g (43%) of the title compound.

MH$^+$=581

TLC rf: 0.26 (CHCl$_3$/MeOH/NH$_4$OH, 70:30:7)

IR (cm$^{-1}$) 3350 (NH); 1700 (C=O); 1250 (P=O); 1100, 1050 (C—O—C and P—O—C)

$^1$H-NMR: CD$_3$OD, δ (TMS), 500 MHz 2.3 (s, 3H, NCH$_3$); 2.45 (m, 3H, NCH$_2$); 2.6 (m, 2H, CH$_2$N); 2.75 (d, 3H, CONHCH$_3$); 3.4 [s, 9H, N$^+$(CH$_3$)$_3$]; 3.7 (m, 2H, CH$_2$N$^+$); 3.95 (m, 2H, CH$_2$OP); 4.3 (m, 2H, POCH$_2$); 5 (m, 1H, HCOCON); 7 (1H, CONH).

EXAMPLE 8

3-(N-methyl octadecylamino)-2-[N,N-(dimethyl)carbamoyloxy]propan-1-ol phosphocholine Compound of the formula Ib wherein $R_1=CH_3$, $R_2=C_{18}H_{37}$,

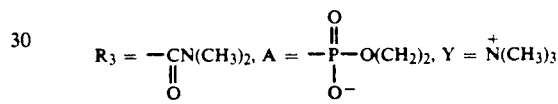

$$R_3 = -\overset{O}{\underset{\|}{\overset{\|}{C}}}N(CH_3)_2, \quad A = -\overset{O}{\underset{\underset{O^-}{|}}{\overset{\|}{P}}}-O(CH_2)_2, \quad Y = \overset{+}{N}(CH_3)_3$$

This compound was prepared by the same procedure as described in example 7 but starting with 3-(N-methyl octadecylamino) 2-[N,N-(dimethyl)carbamoyloxy]propan-1-ol instead of 3-(N-methyl octadecylamino)-2-methylcarbamoyloxy propan-1-ol.

Yield: 40% MH$^+$=594

TLC rf: 0.3 (CHCl$_3$/MeOH/NH$_4$OH, 70:30:7, v/v/v)

IR (cm$^{-1}$) 1700 (C=O); 1250 (P=O); 1100,1050 (C—O—C, P—O—C)

$^1$H-NMR: CD$_3$OD, TMS, 500 MHz, δ 2.2 (s, 3H, NCH$_3$); 2.35 (m, 2H, NCH$_2$); 2.55 (m, 2H, CH$_2$N); 2.85 [d, 6H, CON(CH$_3$)$_2$]; 3.25 [s, 9H, N$^+$(CH$_3$)$_3$]; 3.55 (m, 2H, CH$_2$N$^+$); 3.9 (m, 2H, CH$_2$OP); 4.25 (m, 2H, POCH$_2$); 4.95 (m, 1H, HCOCON).

EXAMPLE 9

3-(N-methyl-octadecylamino)-1-methoxy-propan-2-ol phosphocholine

Compound of the formula Ic wherein $R_1=CH_3$, $R_2=C_{18}H_{37}$,

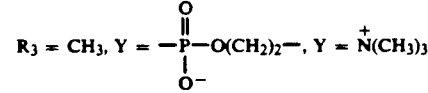

$$R_3 = CH_3, \quad Y = -\overset{O}{\underset{\underset{O^-}{|}}{\overset{\|}{P}}}-O(CH_2)_2-, \quad Y = \overset{+}{N}(CH_3)_3$$

This compound was obtained by the procedure described in example 1 but starting from 3-(N-methyl-octadecylamino)-1-methoxy-propan-2-ol (IIc) instead of 2-(N-methyl-octadecylamino)-3-methoxy-propanol (IIa).

TLC rf: 0.24 (CHCl$_3$/MeOH/NH$_4$OH, 70:30:7, v/v/v)

Yield: 35%
mp: 248° C.
IR (cm$^{-1}$) 1240 (P=O); 1100 (C—O); 1040 (P—O)
$^1$H-NMR: 500MHz, CD$_3$OD, (TMS) δ 0.82 (t,3H,CH$_3$); 1.25 [s,30H,(CH$_2$)$_{15}$]; 1.45 (t,2H,N—CH$_2$CH$_2$); 2.2 (s,3H,NCH$_3$); 2.35 (m,2H,NCH$_2$); 2.55 (m,2H,CH$_2$N); 3.2 [s,9H,N$^+$2(CH$_3$)$_3$]; 3.35 (s,3H,OCH$_3$); 3.5 (m,2H,CH$_2$OCH$_3$); 3.6 (m,2H,CH$_2$N+); 4.25 (m,2H,POCH$_2$); 4.3 (1H,CHOP).

EXAMPLE 10

1-octadecylamino 3-methoxy propan-2-ol phosphocholine

Compound of the formula Ic wherein R$_1$=H, R$_2$=C$_{18}$H$_{37}$, R$_3$=CH$_3$,

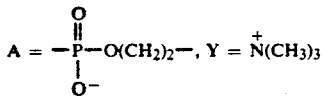

$$A = -\overset{O}{\underset{O^-}{\overset{\|}{P}}}-O(CH_2)_2-, \quad Y = \overset{+}{N}(CH_3)_3$$

This compound was obtained by the procedure as described in example 6, comprising the preparation and the deprotection of 1-N,N-(benzylsulfonyloctadecyl-)amino 3-methoxy propan-2-ol phosphocholine.
M=550
TLC rf: 0.20 (CHCl$_3$/MeOH/NH$_4$OH, 70:30:7, v/v/v)
$^1$H-NMR: 500 MHz, CD$_3$OD, (TMS) δ 2.9 (m, 3H, NH and NCH$_2$); 3.1 (m, 2H, CH$_2$N); 3.4 [s, 9H, N$^+$(CH$_3$)$_3$]; 3.55 (s, 3H, OCH$_3$); 3.7 (m, 2H, CH$_2$N$^+$); 3.85 (m, 2H, CH$_2$OMe); 4.5 (m, 2H, POCH$_2$); 4.6 (m, 1H, CHOP).

Toxicity

The toxicity of the compounds of the invention has been determined per os on mice by usual methods. Their LD$_{50}$ values are higher than 650 mg/kg.

Pharmacology

The compounds of the invention have been examined for their ability to inhibit in vitro tumor cell proliferation.

They inhibit HL60 and A.427 tumor cell proliferation after 24 hours.

HL60: promyelocytic leukemia cell line
A.427: lung carcinoma cell line

They show a cytostatic effect at the dose of 0.02 mM which is not a toxic dose for the two human tumor cell lines. Overall, the lung carcinoma cell line was more sensitive than the promyelocytic leukemia cell line.

The effect of the compounds of the invention on long-term proliferation has been more precisely described above.

All of the examples of the invention have been tested and compared with two related compounds of the prior art:
the 1-O-octadecyl- 2-O-methylglycero- 3-phosphocholine (Et-18-OCH$_3$ or methoxy PAF ; Andreesen, 1988),
the 3-octadecyl-1-O-tetradecyl-propan-1,2-diol-2-O-phosphocholine [compound (D)].

For this study, a colon adenocarcinoma cell line, called HT.29, has been used; they are anchorage-dependent cells.

The HT.29 cells were grown in McCoy medium (Flow Labs), supplemented with 10% foetal bovine serum (FBS; Gibco). The growth media contained 100 U/ml of penicillin and 100 μg/ml of streptomycin (Flow Labs).

The compounds of the invention and the compounds (D) and Et-18-OCH$_3$, were dissolved in a solution containing 60% ethanol and 40% phosphate buffer saline (PBS; Flow Labs).

Serial dilutions were prepared in PBS. The dose tested was 0.02 mM. The treatment time lasted 24 hours at 37° C.

The effect of the compounds of the invention on long-term cell proliferation and survival, has been evaluated by studying the plating efficiency and colony morphology of HT.29. To carry out this study, 5.10$^2$, HT.29 cells, previously treated with the different compounds of the invention for 24 hours, were seeded into 25 cm$^2$ growth area tissue culture flasks.

These cell cultures were then incubated at 37° C. for 15 days. At the end of this incubation time, the cell cultures were rinsed twice with PBS, fixed with 70% ethanol for 30 minutes and stained for the same length of time with 10% Giemsa (Sigma Chemicals).

The results are expressed as 'relative plating efficiency (P.E.)' values calculated as follows:

$$P.E. = \frac{\text{Number of colonies formed}}{\text{Number of cells plated}} \times 100$$

and summarized in the following tables.

It has been found that the colonies formed after treatment of compounds of the invention, have lost their regular profile, have a lower reactivity to the Giemsa stain and, overall, their size is smaller than that of the untreated colonies.

| COMPOUNDS | P.E. (%) | COMPOUNDS | P.E. (%) |
|---|---|---|---|
| Control | 100 ± 4.3 | EX 5 | 20.6 ± 1.7** |
| Et-18-OCH3 | 39 ± 1.5 | EX 6 | 26.4 ± 1.7** |
| (D) | 34 ± 2.3** | | |
| EX 1 | 21.9 ± 1.0*** | EX 7 | 22.3 ± 2.2*** |
| EX 2 | 24.3 ± 1.4** | EX 8 | 19.9 ± 0.9*** |
| EX 3 | 27.1 ± 2.1* | EX 9 | 20.2 ± 1.2** |
| EX 4 | 45.6 ± 3.0 NS | EX 10 | 25.4 ± 2.7* |

The statistical symbols refer to the comparison between each compound with the reference Et-18-OCH$_3$. The different symbols: NS, *,  and * mean that the result is respectively not significative, significative, very significative and highly significative.

Posology

In human therapy, the compounds of the invention are preferably administrated by I.V. route. Usual posology is from 2.5 to 5 mg per dm$_2$ area of the tumor per diem, three to six days per month in slow perfusion.

We claim:
1. Glycerol derivatives of general formulae Ia, Ib and Ic

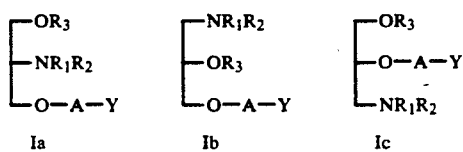

Ia      Ib      Ic wherein:

R₁ represents a hydrogen atom or a lower alkyl group up to C₅;

R₂ represents a straight chain or branched chain alkyl group having from 10 to 24 carbon atoms;

R₃ represents an aryl or an alkyl radical, CONH-alkyl, CON-dialkyl, each alkyl group having from 1 to 6 carbon atoms;

A stands for:

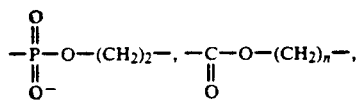

$$-\underset{\underset{O^-}{\overset{O}{\|}}}{P}-O-(CH_2)_2-, \quad -\overset{O}{\underset{\|}{C}}-O-(CH_2)_n-,$$

-continued $$-\overset{O}{\underset{\|}{C}}-NH-(CH_2)_n-,$$

n being an integer of from 2 to 10;

Y represents the following quaternary ammonia: ammonium, alkylammonium, dialkylammonium, trialkylammonium, each alkyl group having from 1 to 6 carbon atoms, or a saturated or unsaturated heterocycle containing nitrogen atom as a hetero atom, and therapeutically acceptable salts thereof.

2. A therapeutic composition for treatment of tumors comprising as an active ingredient any one of the compounds of claim 1 or a combination of two or more of the compounds of claim 1 in a pharmaceutically acceptable diluent or carrier, the said active ingredient being present in an amount to be effective in the treatment of tumors.

* * * * *

UNITED STATES PATENT AND TRADEMARK OFFICE
CERTIFICATE OF CORRECTION

PATENT NO. : 5,116,992
DATED : May 26, 1992
INVENTOR(S) : Pierre Braquet et al.

It is certified that error appears in the above-identified patent and that said Letters Patent is hereby corrected as shown below:

Column 1, lines 30-34, delete the chemical formulas set forth therein and substitute therefor the following:

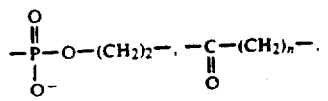

Column 2, line 47, after "4a" insert --:--.

Column 2, lines 50-55, delete: 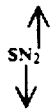

and substitute therefore --$S_N2$--.

Column 5, line 5, change "CCNRR'" to --OCNRR'--.

Column 5, line 14, change "CCNRR'" to --OCNRR'--.

Column 18, line 56, change "$dm_2$" to --$dm^2$--.

UNITED STATES PATENT AND TRADEMARK OFFICE
CERTIFICATE OF CORRECTION

PATENT NO. : 5,116,992

DATED : May 26, 1992

INVENTOR(S) : Pierre Braquet et al.

It is certified that error appears in the above-identified patent and that said Letters Patent is hereby corrected as shown below:

Column 19, lines 16-19, delete the chemical formulas set forth therein and substitute therefor the following:

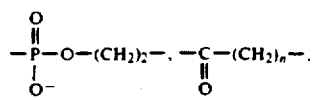

Signed and Sealed this

Sixth Day of July, 1993

Attest:

MICHAEL K. KIRK

Attesting Officer

Acting Commissioner of Patents and Trademarks